United States Patent [19]

Filka et al.

[11] 4,446,275

[45] May 1, 1984

[54] SORBENT FOR SACCHARIDES, GLYCOPROTEINS AND POLYESTERS COMPRISING A LECTIN COVALENTLY BONDED WITH A VEHICLE AND METHOD FOR PREPARATION THEREOF

[75] Inventors: Karel Filka; Jiri Coupek; Jan Kocourek, all of Prague, Czechoslovakia

[73] Assignee: Prirodovedecka fakulta University Karlovy, Prague, Czechoslovakia

[21] Appl. No.: 369,232

[22] Filed: Apr. 16, 1982

Related U.S. Application Data

[63] Continuation-in-part of Ser. No. 143,752, Apr. 25, 1980, abandoned.

[51] Int. Cl.$^3$ .................. C12N 11/16; C12N 11/12; C12N 11/06
[52] U.S. Cl. .................. 525/54.1; 210/502.1; 435/174; 435/179; 435/181
[58] Field of Search .................. 524/27, 200, 300; 525/54.1; 435/174, 177, 178, 179, 180, 181; 210/502

[56] References Cited

U.S. PATENT DOCUMENTS 3,914,183 10/1975 Johansson et al. .................. 435/180
3,947,352 3/1976 Cuatrecasas et al. .................. 435/178
4,038,140 7/1977 Jaworek et al. .................. 435/178

FOREIGN PATENT DOCUMENTS 55-156694 6/1980 Japan .................. 435/180

OTHER PUBLICATIONS

*Acta Chem. Scand.,* vol. 24, No. 5, 1970/pp. 1839–1841, short communication, Aspberg, Kåre et al., "Group Specific Adsorption of Glycoproteins".

*Primary Examiner*—John Kight, III
*Assistant Examiner*—Nathan M. Nutter

[57] ABSTRACT

The invention relates to selectively acting polymeric sorbents or saccharides, glycoproteins and saccharide containing polymers. In accordance with the invention, lectins are covalently bonded on vehicles selected from among, oxidized glycosylated hydroxyalkylacrylates or hydroxyalkylmethacrylates, and polyvinyl alcohol. These vehicles are comparable to known materials based on polysaccharides with bonded-on lectins, especially as far as the absorption power of the sorbent is concerned. The preferred process for preparing such sorbents is substantially easier than the hitherto used ones since it does not require specific measures to be taken in the work with highly toxic activating agents, and enables a simple control of conversion degree of the bonding reaction while achieving a relatively high reproducibility. Apart from this, unoxidized saccharide molecules bonded on the vehicle make it hydrophilic, or at least raise its original hydrophility.

1 Claim, No Drawings

SORBENT FOR SACCHARIDES, GLYCOPROTEINS AND POLYESTERS COMPRISING A LECTIN COVALENTLY BONDED WITH A VEHICLE AND METHOD FOR PREPARATION THEREOF

This application is a continuation-in-part of copending application, Ser. No. 143,752, filed Apr. 25, 1980, now abandoned.

This invention relates to sorbents for saccharides, glycoproteins and saccharides containing polymers.

Proteins which evidence the ability to selectively complex with sugars, polysaccharides and glycoproteins, commonly known as lectins, have heretofore been isolated from a plurality of vegetable and animal sources. These lectins are commonly characterized not only by their origin but also by their specific affinity for sugars and derivatives thereof.

The linking of lectins upon an appropriate vehicle gives rise to specific absorbents for saccharides, provided that an active sorption center in the lectin molecule is maintained intact during the linking reaction, so indicating that it must not be blocked. These sorbent-containing lectins are suitable for use in diverse applications in both analytic and preparative affinity chromotography as well as in selective precipitation techniques availed of in isolating biologically active fractions.

Heretofore, the lectins have been linked upon polysaccharides of dextrane, or the agarose type by the cyanogen bromide method and have found application in many isolation techniques for separation of glycoproteins (see K. Aspberg and J. Porath, Acta Chem. Scand. 24, 1970, 1839), for the separation of dextrans (see K.O. Lloyd, Arch.Biochem.Biophys. 137, 1970, 460) and the separation of cells (see G. H. Edelman, U. Rutishauser and C. F. Millete, Proc. Nat.Acad.Sci. U.S.A., 68, 1971, 2153). Such processes are advantageous due to their relatively high selectivity and speed. However, polysaccharide vehicles of dextrane, of the polysaccharide type exhibit certain disadvantageous properties such as a significant differential swelling capacity in solutions with variable ionic strength and pH value, and a relatively low mechanical strength of particles. As a result, workers in the art have encountered difficulties with the choking of columns filled with such materials at elevated pressure and through-flow rates of the mobile phase. Last, but not least, some obstructive factors can be seen in a relatively low resistance to hydrolysis and to the action of microorganisms. The mode of lectin molecule linkage by using the cyanogen bromide method makes it necessary to employ a highly toxic agent, the efficiency of which is relatively low. Additionally, the bond arising in the aforementioned cyanogen bromide process is not sufficiently stable for some purposes, which means that it is prone to a gradual hydrolytic degradation accompanied by a reduction of sorbent capacity.

In accordance with the present invention, these prior art limitations are effectively obviated by attainment of a covalent linkage of sugar molecules using the process disclosed in the Czechoslovak Inventor's Certificate No. 206,823 (CS Appln. PV 2891-77). This process makes use of an acid-catalyzed reaction of saccharides with polymers containing hydroxyl groups in dioxane, or in tetrahydrofuran. For this reason, there may be used, apart from hydrophilic synthetic polymers (cacroporous hydroxyalkylacrylates and hydroxyalkylmethacrylates, partially hydrolysed cross-linked polyvinyl acetate etc.), a plurality of natural or semisynthetic hydrophilic polymers (polydextranes, agarose polymers, cellulose and other) since the actual reaction must be carried out in an anhydrous medium which excludes a possible hydrolysis of glycosidic or peptidic bonds.

The resultant glycosyl derivatives of polymers are subjected to oxidation by a periodate, the action of which results in the degradation of the C-C bond between two carbon atoms with a vicinal bond of hydroxyls in the molecules of covalently bonded saccharides while two aldehydic groups arise which latter are highly reactive. The polymer activated by oxidation reacts in the next stage with lectin under formation of a Schiff's base. The speed of this reaction depends upon the concentration of components and on the temperature, and is strongly influenced by the pH value of the reaction medium. The non-reacted aldehydic active groups are reduced by the action of sodium borohydride. The thus arisen sorption, or precipitation substances are characterized by their high capacities. It is an object of the invention to provide selectively acting polymer sorbents for saccharides, glycoproteins and polymers containing saccharides.

In accordance with the inventive techniques, lectins are covalently bonded upon vehicles selected from among oxidized glycosylated hydroxyalkylacrylates of hydroxyalkylmethacrylates, and polyvinyl alcohol.

A convenient method for preparing such sorbents involves oxidizing polymers containing covalently bonded saccharides by the use of sodium or potassium periodate whereupon the thus activated polymers are allowed to react with lectins at a temperature ranging up to 40° C. in buffer solutions having a pH value within the range of 7–12. Aldehydic active groups remaining after the reaction are eliminated by the action of reductants, preferably sodium borohydride.

Analysis of the properties of the products so produced reveals the substances of the invention that they are comparable with the heretofore known materials on the basis of polysaccharides bonded with lectins by the cyanogen bromide method, the adsorptive sorbent capacity constituting the efficiency criterion. The process of preparing such substances as described is simpler from a technological standpoint, does not require specific safety measures for work with highly toxic activating agents and allows a simple control of conversion grade during the highly reproducible reaction. Moreover, the non-oxidized saccharide molecules bonded on the vehicle give the process a hydrophilic character, or raise its original hydrophility. In this manner, the probability of non-specific interactions between the components of separate systems, if using the sorbents in affinity chromatography, is reduced.

The synthetic matrices based upon copolymerization of hydroxyalkylacrylates, hydroxyalkylmethacrylates and vinyl alcohol represent macroporous rigid structures when synthesis thereof is conducted in the presence of a sufficient amount of cross-linking agent. Carriers of this type, in contradistinction to modified natural polysaccharides evidence minimal swelling characteristics in any type of sorbent and are characterized by permanent porosity in the dry condition. Chemical modification of these carriers occurs on the phase (inner pore surface) which makes this type of carrier analogous to modified carriers based on silica gel or porous glass. This prime property earmarks the macroporous carriers for use in processes employing elevated pressures, high flow rates or very high chromatographic columns.

A different type of the same copolymer may be obtained when a lesser amount of a cross-linking reagent is used for copolymerization. Under these circumstances, the copolymer so produced evidences pronounced hydrophilic properties.

The two types of copolymers described differ significantly in chemical composition, matrix structure and related physical and physicochemical porperties from polysaccharide and polysaccharide-acrylamide based carriers. Thus, for example, matrices prepared in accordance with the invention do not contain (as contrasted with the polysaccharides) sugar in their basic chemical structure but are modified by additional glycosylation and, following such modification and activation with periodate, function as lectin immobilizers.

The foregoing combination of excellent qualities of the basic matrices with the advantageous effects of covalently coupled sugars endows the carriers with certain distinctive properties. These include high mechanical stability, suitability for use at elevated pressures, applicability in chromatographic procedures in high columns, rapid flow rates, substantially higher hydrolytic stability of the matrix and the immobilized lectins, higher resistance against microbial attack, and the ability to obtain carriers in perfect spherical form in a size ranging from 5μm to 2 millimeters, dependent upon the conditions of the polymerization reaction.

Several examples of the present invention are set forth below. It will be appreciated by those skilled in the art that these examples are solely for purposes of exposition and are not to be construed as limiting.

EXAMPLE 1

15 grams of 2-hydroxyethylmethacrylate/ethylenemethacrylate copolymer of 1,000,000 molecular weight exclusion limit, containing 16 percent of covalently bonded galactose (α-D-Gal Separon HEMA-1000) was swelled in 150 milliliters of water for 20 hours. After the liquid substance had been sucked off, there was added an amount of 346 milliliters of 0.1 M NaIO$_4$. Oxidation was effected for 100 minutes at 25° C. The product was then washed through with water up to the negative reaction to oxidants (Mn$^{++}$), equilibrated by a buffer in which the binding of lectin was carried out (acetate buffers with various pH values), and used for the next linkage reaction.

140 milliliters of an acetate buffer (pH 7.8) was employed for dissolving 2.4 grams of lectin from Canavalia ensiformis DC (concanavalin A); to the solution there was added the equilibrated oxidized vehicle from the previous stage in the form of a thick pulp together with 250 milligrams of D-glucose. The mixture was agitated in a refrigerator for 24 hours at 4° C. Thereupon, 25 milligrams of NaBH$_4$, and after 20 minutes another 25 milligrams of NaBH$_4$, were added thereto. The mixture was then contacted with sodium borohydride for a total period of 40 minutes. Thereafter, the sorbent was washed with an acetate buffer (pH 7.3) and then washed three times with 200 milliliters of Tris HCl buffer in one mole of NaCl (pH 8) and in acetate buffer in one mole NaCl (pH 4). The thus treated sorbent was transferred to a column and washed with a buffer in which a sorption effect relative to saccharide derivatives was proved. The amount of bonded concanavalin was 15 milligrams per one gram of dry vehicle.

The effect of bonded lectin was proved by the sorption of synthetic polymer (acrylamide) containing covalently bonded saccharides (glucose, galactose) in the following process:

To a column of one gram vehicle with bonded lectin, after equilibration with an acetate buffer (pH 7.3), 0.3427 gram of a soluble polyacrylamide polymer containing 9.4%, by weight, of glucose in a start buffer was applied. During the elution of 102 milliliters of buffer, the sugar content was examined up to the zero value. To the column, there was then supplied a solution of 0.5 mole methyl α-D-glucopyranoside (30 milliliters) whereupon the column was washed with the start buffer of 7.3 pH. The eluate was recaptured, dialyzed and lyophilized. 0.016 gram of polymer was determined by gravimetry. On the basis of substance balance, there was chromatographically determined 3.1% loss on the glycosylated polyacrylamide standard.

EXAMPLE 2

A sorbent was prepared and processed in accordance with EXAMPLE 1. Its effect was proved by selective sorption of ovalbumin whereupon a repeated use was estimated. One gram of sorbent of EXAMPLE 1 together with concanavalin A bonded thereonto was equilibrated in Tris HCl buffer pH (7.8)+0.15 M NaCl. To the column, there was applied 49 milligrams of ovalbumin in 5 milliliters of start buffer, and the system washed with the buffer up to the negative reaction to proteins (UV absorbance 280 nm) under simultaneous eluate recapture. Thereafter, a 0.1 M solution of methyl α-D-glucopyranoside (50 milliliters) was applied thereto. The eluate was recaptured, dialyzed and lyophilized. The yield in the eluate was 7.8 milligrams, the unbonded protein content determined to be 40 milligrams and the losses 2.44%.

The column was then washed with 20 milliliters of Tris HCl buffer (pH 7.8)+1 M NaCl and by 20 milliliters of an acetate buffer+1 M NaCl (pH 4), equilibrated by Tris HCl buffer+0.15 M NaCl (pH 7.8), and the entire process repeated.

In the second cycle, the protein content in the eluant after washing with methyl α-D-glucopyranoside was 7.6 milligrams, in the third 7.8 milligrams and in the fourth 7.6 milligrams.

EXAMPLE 3

A sorbent was prepared in accordance with the procedure of EXAMPLE 1, except that in lieu of a copolymer having an exclusion limit of one mil. dalton, there were used as a vehicle for the copolymer 2-hydroxyethylacrylate together with ethylenedimethacrylate having a molecular weight exclusion limit of 300,000. After the effect had been proved by glycosylated polyacrylamide, a 4.6 percent loss was ascertained (0.3470 grams applied, 0.0154 grams found in the eluant). The starting sorbent contained 18%, by weight, of covalently bonded glucose.

EXAMPLE 4

For bonding the lectin obtained out from Ricinus communis an oxidized vehicle (see EXAMPLE 3) was used. 1.9 grams of lectin was dissolved in 70 milliliters of acetate buffer (pH 7.3) containing 220 milligrams of galactose whereupon 10 grams of oxidized vehicle was added to the solution. The elimination of non-reacted aldehydic active groups was effected with 25 milligrams of NaBH₄; the reaction time was the same as set forth in EXAMPLE 1.

The effect was tested by polyacrylamide with 9%, by weight, sugar content; 0.3412 g applied, 0.0154 grams yield in the eluant, 3.8% loss.

EXAMPLE 5

The bond of lectin out from Ricinus communis was effected analogously as described in EXAMPLE 4, except that the molecular weight exclusion limit was 300,000 dalton.

To prove the effect by polyacrylamide with bonded glucose, there was applied to one gram of the column 0.3400 gram of polymer; yield in the eluant—0.0171 gram, loss—4.75%

EXAMPLE 6

4.0 grams of polyvinyl alcohol having a molecular weight of 125,000 and a hydrolysis degree of 87–89 percent and substituted with D-glucose according to the Czechoslovakian Inventor's Certificate No. 195,044, was oxidized in 100 milliliters of 0.1 M NaIO₄ for one hour at ambient temperature. Hereafter, the reaction mixture was diluted to 250 milliliters and allowed to dialyze against distilled water. After removal of periodate from the reaction mixture by dialysis, the product was ready for analysis.

EXAMPLE 7

A sorbent was prepared in accordance with the procedure of EXAMPLE 1 with the exception that a hydroxyethylacrylate/ethylenediacrylate copolymer having a molecular weight exclusion limit of 500,000 was used instead of an ethylene dimethacrylate/hydroxyethyl methacrylate copolymer. The effect of glycosylated polyacrylamide by sorption was found to be a 5.3 percent loss.

We claim:

1. Sorbent for saccharides, glycoproteins and polymers comprising a lectin covalently bonded with a vehicle selected from the groups consisting of (a) oxidized glycosylated hydroxyethylacrylates, (b) oxidized glycosylated hydroxyalkyl methacrylates, and (c) oxidized glycosylated polyvinyl alcohol.

* * * * *